United States Patent [19]

Hosztafi et al.

[11] Patent Number: 5,232,926

[45] Date of Patent: Aug. 3, 1993

[54] MORPHINANE-SKELETONED HYDRAZONE DERIVATIVES

[75] Inventors: Sándor Hosztafi, Monostorpályi; Sándor Makleit; László Szilágyi, both of Debrecen; Kálmány Zsupán, Tiszavasvári, all of Hungary

[73] Assignee: Alkaloida Vegyészeti Gyár Rt., Tiszavasvári, Hungary

[21] Appl. No.: 957,642

[22] Filed: Oct. 6, 1992

Related U.S. Application Data

[63] Continuation of Ser. No. 755,590, Sep. 4, 1991, abandoned, which is a continuation of Ser. No. 544,040, Jun. 26, 1990, abandoned, which is a continuation of Ser. No. 361,809, May 30, 1989, abandoned, which is a continuation of Ser. No. 140,905, Dec. 30, 1987, abandoned, which is a continuation of Ser. No. 855,227, Apr. 22, 1986, abandoned.

[51] Int. Cl.⁵ ................. C07D 489/08; A61K 31/485
[52] U.S. Cl. ..................................... 514/282; 546/45; 546/46
[58] Field of Search ............... 546/45, 46; 514/282

[56] References Cited

U.S. PATENT DOCUMENTS

| | | | |
|---|---|---|---|
| 2,797,221 | 6/1957 | Gates, Jr. | 546/44 X |
| 4,608,376 | 8/1986 | Pasternak | 514/282 |
| 4,678,779 | 7/1987 | Meyers et al. | 514/176 |
| 4,730,048 | 3/1988 | Portoghese | 546/45 |
| 4,803,208 | 2/1989 | Pasternak | 514/282 |
| 4,806,556 | 2/1989 | Portoghese | 546/44 |

FOREIGN PATENT DOCUMENTS

0077521 4/1983 European Pat. Off. ............ 514/282

OTHER PUBLICATIONS

Borsodi, et al., "Advances in the Biosciences", vol. 75, Pergamon Press (1989), pp. 25–28.
Hoztafi et al., Chem. Abstr vol. 114 Entry 62427a (1990).

(List continued on next page.)

Primary Examiner—Donald G. Daus
Attorney, Agent, or Firm—Schweitzer Cornman & Gross

[57] ABSTRACT

The present invention relates to novel morphinane-skeletoned compounds of the formula (I)

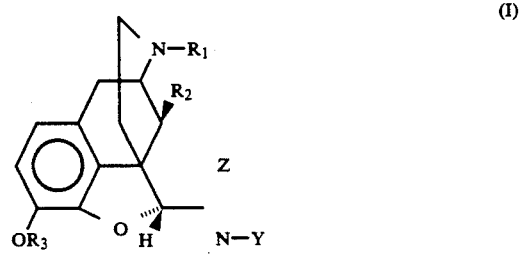

wherein Y in-NH phenyl or —NH dintro phenyl, Z is —CH$_2$— CH$_2$, R$_2$ is hydroxyl and R$_3$ is H or methyl, the steric isomers and the pharmaceutically acceptable salts thereof, a novel process for producing the same and pharmaceutical compositions comprising the same as active ingredients.

The novel compounds can be used in the therapy as analgetic or morphine-antagonistic agents.

2 Claims, No Drawings

OTHER PUBLICATIONS

Hoztafi et al. Chem. Abstr vol. 111 entry 23761y (1988).
Hoztafi et al. Chem. Abstr. vol. 108 entry 187032a abstract Hungary 4 06666 (1987).
Bentley, "The Chemistry of the Morphine Alkaloids", Clarendon Press, Oxford, 1954, pp. 179-182, 259, 262.
Goto, et al., Chemical Abstracts, vol. 52, 5440i-5441e (1958).
Sargent, et al., Chemical Abstracts, vol. 53, 14133a-14134c (1959).
Liu, et al., Chemical Abstracts, vol. 100, 121411b (1984).
Kolb, et al., Chemical Abstracts, vol. 101, 152154v (1984).
Szücs, et al., MTA Biol. Oszt. Közl., vol. 25 p. 655 (1982).
Stein, Pharmazie, vol. 10, pp. 180-186 (1955).
Speyer, et al., Berichte, vol. 57, pp. 1422-1427 (1924).
Galetta, et al., Life Sciences, vol. 31, pp 1389-1392 (1982).
Pasternak, Life Sciences, vol. 31, pp. 1303-1306 (1982).
Weiss, et al., J. Org. Chem., vol. 14, pp. 194-203 (1949).
Hahn, et al., J. Neuroscience, vol. 2, No. 5, pp. 572-576 (1982).
Pasternak, J. Med. Chem., vol. 23, pp. 674-676 (1980).
Kolb, et al., J. Org. Chem., vol. 49, pp. 3824-3828 (1984).
Kolb, et al., Life Sciences, vol. 33, suppl. 1, pp. 419-422 (1983).
Hahn, et al., Life Sciences, vol. 31, pp. 1385-1388 (1982).

MORPHINANE-SKELETONED HYDRAZONE DERIVATIVES

This is a continuing application of U.S. Ser. No. 755,590, filed on Sep. 4, 1991, which is a continuing application of U.S. Ser. No. 544,040, filed on Jun. 26, 1990, which is a continuing application of U.S. Ser. No. 361,809, filed on May 30, 1989, which is a continuing application of U.S. Ser. No. 140,905, filed on Dec. 30, 1987, which is a continuing application of U.S. Ser. No. 855,227, filed on Apr. 22, 1986, all now abandoned.

TECHNICAL FIELD

The present invention relates to novel morphinane-skeletoned hydrazone derivatives of the formula (I)

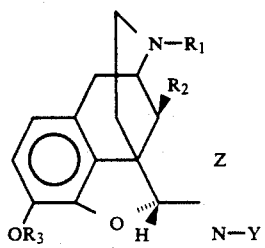

(I)

and the pharmaceutically acceptable salts thereof, a novel process for producing the same, pharmaceutical compositions comprising the same as active ingredient and their use in the therapy as analgetic or morphine-antagonistic agents.

BACKGROUND ART

The reaction of 14-hydroxy dihydromorphinone, Naloxon and Naltrexon with hydrazine was reported first time in 1980 (G. W. Pasternak; E. F. Hahn: J. Med. Chem. 23 674 (1980)). When the condensation products thus formed, the hydrazones were submitted to pharmacological examinations, it turned out that the original activity A 3690-123-HB1 of the starting molecules (analgetic or morphine-antagonistic activity) is retained, however, the duration of the effect of the compounds significantly increased.

It was established in the course of the further examinations that the activity of the hydrazone derivatives can be attributed to the formation of ketazines [E. F. Hahn, M. Carroll-Buatti; G. Pasternak: J. Neuroscience 2 (5) 572 (1982); E. F. Hahn, G. Pasternak: Life Sci. 31 1385 (1982); S. Saletta, G. S. F. Ling, L. Wolfin, G. W. Pasternak: Life Sci. 31 1389 (1982)]. The authentic ketazines selectively link to opiate receptors in vitro 20–40 times better, than the corresponding hydrazone analogues.

When the $^{13}$C-NMR analysis of the hydrazones was carried out, it was found, that they are the mixture of syn and anti isomers, wherein the sterically less crowded anti isomer is the dominant [V. M. Kolb, J. R. Gober: Life Sci. 33 Suppl. I 419 (1982); V. M. Kolb; D. H. Hua: J. Org. Chem. 49 3824 (1984)]. According the above authors only the anti isomer product was formed in the reaction of oxymorphone, Naloxon, and Naltrexon with N,N-dimethyl hydrazine.

Hungarian researchers prepared Naloxone phenylhydrazine [Szücs M., Tóth G., Benyhe S.: MTA Biol. Oszt. Közl. 25 655 (1982)], while Chinese authors described the hydrazones and N,N-dimethyl hydrazones of 14-hydroxy morphinone and 14-hydroxy codeinone [M. Liu, C. Chi, Y. Gvo, C. Zhu: Yaoxue Xuebao 18 475 (1983); C. A. 100 (15) 121411b (1984)].

As the hydrazone derivatives are very interesting from pharmacological point of view, therefore our experiments were extended to further morphine-skeletoned ketons (dihydrocodeinone, dihydromorphinone, dihydrotebainone, codeinone, 14-hydroxy codeinone, 14-hydroxy dihydrocodeinone).

In the prior art the hydrazone derivative of more morphine-skeletoned ketone has been described. They were prepared mainly for analytical purposes, as the semicarbazones, phenylhydrazones, 2,4-dinitro phenylhydrazones can be well crystallized.

The preparation of the hydrazone of 14-hydroxy codeinone and 14-hydroxy dihydrocodeinone was reported even in 1924 [E. Speyer, K. Sarre: Ber. 57 1422 (1924)].

DETAILED DESCRIPTION OF THE INVENTION

The novel compounds of the invention are represented by the formula (I)

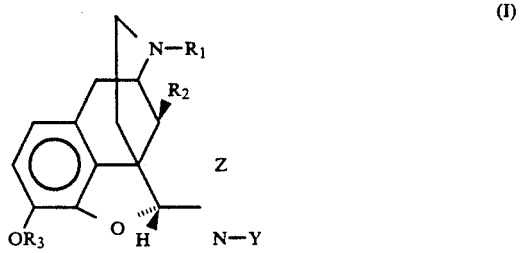

(I)

wherein
Z represents $CH_2$-$CH_2$ or —CH=CH-,
$R_1$ stands for methyl, —$CH_2CH$=$CH_2$,

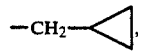, $R_2$ is hydrogen or hydroxy,
$R_3$ is hydrogen or methyl,
Y stands for $NH_2$, —NH-$CONH_2$, —NH-$CSNH_2$, —$NHC_6H_5$, —NH-$C_6H_3(NO_2)_2$; —$NHCOC_6H_5$, —NH-$SO_2C_6H_4$-$pCH_3$,
   the dotted line represents an optional bond, with the following provisions:
when Z represents —$CH_2$-$CH_2$—, $R_2$ represents hydrogen, $R_3$ represents methyl, then $Y_1$ must be different from —NH-$CONH_2$, —$NHCOC_6H_5$, —NH-$C_6H_3(NO_2)_2$,
when Z represents —CH=CH—, $R_2$ represents hydrogen and $R_3$ represents methyl, then Y must be different from —NH-$CONH_2$, —NH-$C_6H_3(NO_2)$, and
when Z represents —$CH_2$-$CH_2$— or —CH=CH—, $R_2$ represents hydroxy, $R_3$ represents methyl, then Y must be different from —$NHC_6H_5$,
when Z is —$CH_2$-$CH_2$—, $R_2$ is hydrogen, $R_3$ is methyl and the dotted line represents a bond, Y must be different from —NH-$CONH_2$.

The present invention also covers the stereoisomers and the pharmaceutically acceptable salts of the above compounds.

The preferred pharmaceutically acceptable salts are inorganic or organic, e.g. the salts formed with hydrochloric, sulfuric, phosphoric acid or tartaric, fumaric, malic, acetic, formic acid.

According to the invention the compounds of the formula (I), wherein

Z represents $CH_2$-$CH_2$ or —CH=CH—,
$R_1$ stands for methyl, —$CH_2CH$=$CH_2$,

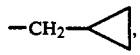, $R_2$ is hydrogen or hydroxy,
$R_3$ is hydrogen or methyl,
Y stands for $NH_2$, —NH-$CONH_2$, —NH-$CSNH_2$, —$NHC_6H_5$, —NH-$C_6H_3(NO_2)_2$; —$NHCOC_6H_5$, —NH-$SO_2C_6H_4$-$pCH_3$ can be prepared by reacting a morphinane-skeletoned ketone of the formula (II)

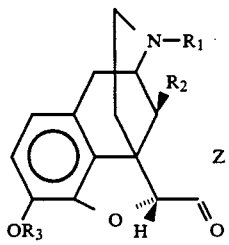

wherein Z, $R_1$, $R_2$ and $R_3$ are the same as defined hereinabove, the dotted line represents an optional bond, with a compound of the formula (III)

$NH_2$-Y              (III)

wherein Y is the same as defined hereinabove.

The invention is based on the recognition that the hydrazone derivatives of the formula (I), which are the mixture of stereoisomers (syn and anti) as crude products, can be prepared in stereochemically uniform form by crystallization and/or chromatographic purification. The present process is suitable for the economic, industrial scale preparation of the analgetic, expectorant or morphine-antagonist morphinane derivatives being important from pharmacological and pharmaceutical points of view in stereochemically uniform form.

The hydrazone derivatives prepared by our process, which chemical structure was verified by modern analytical methods (IR, PMR, MS) had significantly different physical characteristics compared to the literary data. It was found that when alcohol (ethanol or methanol) or dimethyl formamide is used in the reaction as solvent, some ketazine (10 to 20% by weight) is also formed. The structure of the ketazines was also verified besides the instrumental experiments by preparing them from hydrazone and ketone as well.

From the starting ketons codeinone [L. Knorr; H. Hörlein: Ber. 40 2032 (1907)], dihydrotebainone [J. M. Gullend; R. Robinson: J. Chem. Soc. 1923 998] and dihydrocodeinone semicarbazone [A. Stein: Pharmazie 10 180 (1955)] are known from the prior art.

Besides the above compounds the semicarbazone of dihydromorphinone, 14-hydroxy dihydromorphinone, 14-hydroxy codeinone, 14-hydroxy dihydrocodeinone, Naloxon, Naloxon methylether were also prepared.

All of the crude products proved to be composed of two components, but the pure compounds could be isolated by crystallization and/or chromatographic methods. The crude products were the mixtures of the syn and anti isomers according to PMR analysis results.

When the thiosemicarbazones were prepared, the thiosemicarbazones of dihydrocodeinone, dihydromorphinone and 14-hydroxy dihydromorphinone were obtained as a mixture of the stereoisomers, however, they could not be separated. The thiosemicarbazones of 14-hydroxy codeinone and 14-hydroxy dihydrocodeinone were obtained in stereochemically uniform form.

Besides the phenylhydrazone of dihydrocodeinone [A. Stein Pharmazie 10 180 (1955)], 14-hydroxy codeinone and 14-hydroxy dihydrocodeinone [L. J. Sargent, L. H. Schwartzman, L. F. Small: J. Org. Chem. 23 1247 (1958)] known from the prior art dihydromorphinone phenylhydrazone and 14-hydroxy dihydromorphinone phenylhydrazone were also prepared. The separation of the syn and anti isomers of these latter compounds could not be solved. The phenylhydrazone derivatives known from the prior art are stereochemically uniform compounds.

The 2,4-dinitrophenylhydrazone of 14-hydroxy codeinone and 14-hydroxy dihydrocodeinone are homogenous upon examining by thin-layer chromatography while they are stereochemically uniform on the basis of the PMR spectra. When dihydromorphinone and 14-hydroxy dihydromorphinone were used as starting materials always the mixture of the syn and anti isomers could be obtained even the reaction conditions were changed, and these isomers could not be separated.

The dihydrotebainone-2,4-dinitrophenyl hydrazone is uniform on the basis of thin-layer chromatographic analysis, however, the PMR spectra does not form a ground for the decision whether it is the syn or anti isomer.

In order to analyse the PMR spectra, the prior art 2,4-dinitrophenyl hydrazone of codeinone [S. P. Findlay; L. F. Small: J. Am. Chem. Soc. 72 3247 (1950)] and dihydrocodeinone [A. Stein: Pharmazie 10 180 (1955)] were also prepared.

The activity of the compounds of the invention was examined as follows.

The effect of the $10^{-7}$ and $10^{-5}$M concentration of the compounds was examined to tritiated Naloxon bond in rat brain membrane preparates. The results show how the compounds are able to compete for the specific binding positions of the labelled Naloxon. Table I summarizes the measure of the residual tritiated specific bonds of Naloxon.

If the inhibition is high, i.e. the value of the specific bond of the labelled Naloxon is low, the compounds bind to the opiate receptors with high affinity. Those compounds which decreased the specific bond only in low extent (even in a concentration of $10^{-5}$) cannot be considered as significantly bound to the opiate receptors.

A comparative data the tritiated Naloxon bond (concentration: 1 nanomole) was taken as 100% (without excipients).

TABLE I

| Compound | Concentration | |
|---|---|---|
|  | $10^{-7}$ mol | $10^{-5}$ mol |
| Oxycodeinone hydrazone | 92 ± 25 | 13 ± 7 |
| Dihydrocodeinone semicarbazone | 43 ± 4 | 9 ± 7 |
| Dihydromorphinone semicarbazone | 69 ± 13 | 4 ± 6 |
| Dihydrocodeinone phenylhydrazone | 75 ± 9 | 5 ± 1 |

TABLE I-continued

| Compound | Concentration | |
|---|---|---|
| | $10^{-7}$ mol | $10^{-5}$ mol |
| Dihydromorphinone phenylhydrazone | 4 ± 5 | 10 ± 14 |
| Dihydromorphinone dinitrophenyl-hydrazone | 17 ± 2 | 0.5 ± 0.7 |
| Oxymorphone dinitrophenylhydrazone | 33 ± 1 | 1 ± 0.3 |
| Dihydromorphinone thiosemicarbazone | 16 ± 5 | 19 ± 4 |
| Oxymorphone thiosemicarbazone | 37 ± 9 | 0 |

The membrane preparate was prepared according to the following article: G. W. Pasternak, H. A. Wilson, S. H. Snyder: Molecular Pharmacol. 11 340–51 (1975).

The specific radioactivity of the labelled Naloxon was 72.4 Ci/mmole [G. Töth, M. Kramer, F. Sirokmán, A. Borsodi, A. Rónai: J. Label. Comp. Radiopharm. 19 1021 (1976)].

The analgetic activity of the compounds of the invention is summarized in Table II.

TABLE II

| The analgetic activity of the ocmpounds of the invention | | |
|---|---|---|
| | Hot plate test $ED_{50}$ mg/kg.sc. | Tail Flick $ED_{50}$ mg/kg.sc. |
| Dihydromorphinone semicarbazone | 0.085 | 0.13 |
| Oxycodone semicarbazone | 0.58 | 0.45 |
| Dihydroceinone semicarbazone | 0.38 | 0.35 |
| Dihydrocodeinone thiosemicarbazone | 1.7 | 0.6 |
| Oxycodone phenylhydrazone | 0.8 | 1.2 |
| Dihydrocodeinone phenylhydrazone | 2.4 | 2.3 |
| Oxymorphone dinitrophenylhydrazone | 0.37 | 0.27 |
| Dihydromorphinone dinitrophenyl-hydrazone | 0.27 | 0.18 |
| Oxymorphone semicarbazone | 0.9 | 0.9 |
| Morphine | 3.6 | 5.0 |

The compounds wherein a methyl group is bound to the nitrogen are effective analgetic agents, they also have cataleptogenic activity, further potentiate the effect of barbiturates.

The compounds wherein an allyl or cyclopropl-methyl group is bound to the nitrogen, exhibit morphine antagonistic activity.

The invention is illustrated by the following, non-limiting examples.

For the thin-layer chromatographic tests Merck 5554 silica gel 60 $F_{254}$ foils were used. As eluents the following mixtures were applied:

A: chloroform/acetone/diethyl amine = 5:4:1
B: chloroform/methanol/cc. ammonium hydroxide = 90:10:5
C: chloroform/methanol = 9:1
D: benzene/methanol = 8:2

The spots were detected in UV light and by Drag-gendorff reagent.

The PMR spectras were taken in a Bruker W200SY instrument, the chemical shift is given in ppm.

When the steric isomers are characterized, the trans (E) and cis (z) isomer is given compared to the 5β proton.

The mass spectras were taken on a VG-7035 (GC-MS-DS) instrument. The relative intensities are indicated after the mass numbers in parenthesis.

EXAMPLE 1

14-OH-dihydrocodeinionehydrazone 5 ml of 100% hydrazine hydrate are dissolved in 10 ml of dimethyl formamide, then 2.0 g of 14-OH-dihydrocodeinone are added in small portions to the above solution under stirring. The solution is kept over a water bath for 2 hours, then poured into 100 ml of ice water after cooling. The precipitated crystalline substance is filtered off, washed with cold water. 1.5 g of crude product are obtained. The pure fractions obtained after chromatographing on silica gel (eluent: a 9:1 mixture of chloroform and ethanol) (further eluent B) are recrystallized from methanol. M.p.: 192°–4° C.

PMR (CDCl$_3$): 6.6; 6.7 dd (H-1.2; 2H), 5.33 s (NH$_2$; 2H deuterable), 4.93s (H-5β; 1H), 3.8s (OCH$_3$; 3H), 2.35s (N-CH$_3$; 3H) MS (C$_{18}$H$_{23}$N$_3$O$_3$; 329.38) 329(92) 313(10)

EXAMPLE 2

14-OH-dihydrocodeinoneazine 0.6 g of 14-OH-dihydrocodeinone hydrazone and 0.7 g of 14-OH-dihydrocodeinone are dissolved in 30 ml of dry benzene and refluxed for 4 hours. According to thin-layer chromatographic examinations (using eluent B) the hydrazone has transformed, a new spot can be observed besides the spot of the ketone used in an excess. After evaporation off of the benzene, the residue is recrystallized from ethanol twice. 0.25 g of azine are obtained with a melting point of 199°–202° C.

PMR (CDCl$_3$): 6.65 d (H-1.2; 2H), 4.95s (H-5; 1H), 3.75s (OCH$_3$; 3H), 2.35s (N-Me; 3H) MS (C$_{36}$H$_{42}$N$_4$O$_6$; 626.73) 626(8) 611(7) 313(43)

EXAMPLE 3

Dihydrocodeinone hydrazone 4 ml of dry hydrazine are dissolved in 20 ml of dry methanol and 1.0 g of dihydrocodeinone are added in small portions under stirring. After two hours stirring the methanol is evaporated off under vacuo, 50 ml of sodium tetraborate are added to the residue and the solution is extracted with 3×25 ml of chloroform. The chloroform phase is washed with saline and dried over magnesium sulfate. 1.0 g of oily hydrazone comprising a very small amount of azine determined by thin-layer chromatography (using eluent B) is obtained.

Pure hydrazone can be achieved by preparative thin-layer chromatography, but this substance also is a mixture of stereoisomers.

PMR (CDCl$_3$): 6.7dd (H-1.2; 2H), 6.3s (NH$_2$; 1H trans), 5.25 s (H-5β and NH$_2$; 2H cis), 4.9s (H-5β; 1H; trans), 3.8d (OCH$_3$), 2.35s (N-CH$_3$; 3H), The cis/trans ratio is 67/33. MS (C$_{18}$H$_{23}$N$_3$O$_2$-313.38) 313(40) 298(11)

EXAMPLE 4

Dihydromorphinone hydrazone 0.90 g of dihydromorphinone hydrazone are prepared from 1.0 g of dihydromorphinone according to Example 3. The product is a colourless oil, it comprises about 15 to 20% of ketazine according to PMR and TLC experiments. Even the substance purified by preparative thin-layer chromatography does not crystallize and it is a mixture of stereoisomers according to the PMR spectra.

PMR (CDCl$_3$): 6.6–6.7m (H-1.2; cis+trans), 5.3s (NH$_2$+OH), 5.23s (H-5β; 1H cis), 4.85s (H-5β; 1H trans), 2.4s (N-Me; 3H). The cis/trans ratio is 30:70.

EXAMPLE 5

14-OH-codeinone hydrazone

According to the method described in Example 1 1.8 g of 14-OH-codeinone hydrazone were obtained using 2.0 g of 14-OH-codeinone as starting material. Upon examining the endproduct by thin-layer chromatography, two spots were observed. The pure main component can be obtained by preparative thin-layer chromatographic method. The melting point of the title compound is 212°–15° C. after recrystallization from ethanol.

PMR (CDCl$_3$): 6.7dd (H-1.2; 2H), 6.3m (H-7.8; 2H), 5.65d (NH$_2$; 2H deuterable) 5.38s (H-5$\beta$; 1H), 3.75s (OCH$_3$; 3H), 2.4s (N-Me; 3H) MS (C$_{18}$H$_{21}$N$_3$O$_3$-327.37) 327(52) 309(17) 281(41)

EXAMPLE 6

Dihydrocodeinonesemicarbazone

In 50 ml of water 1.25 g of semicarbazide chlorohydrate are dissolved, thereafter 3.0 g of dihydrocodeinone (base) are added. The mixture is heated on a water bath for 30 minutes, thereafter it is made alkaline with concentrated sodium carbonate solution (pH~9-10) after cooling to a temperature of +5° C. The precipitated crystals are filtered, washed with cold water. 3.0 g of crude product are obtained. This crude product comprises two components according to thin-layer chromatographic examination (with eluent mixtures A and B), which are the syn and anti isomers of the title product. After recrystallization from propanol or aqueous ethanol chromatographically homogenous product can be obtained. M.p.: 244°–247° C.

PMR (CDCl$_3$): 9.65s (NH; 1H), 7.8s (NH$_2$; 2H), 6.7dd (H-1.2; 2H), 4.92s (H-5$\beta$; 1H), 3.85s (OCH$_3$; 3H), 2.4s (N-CH; 3H). The 5-$\beta$-H shifts in the crude product comprising 50—50% syn and anti isomers are as follows: 5.2 (cis) and 4.92 (trans) ppm. MS (C$_{19}$H$_{24}$N$_4$O$_3$-356.41) 356(51) 339(38) 297(100) 284(37)

EXAMPLE 7

14-OH-dihydrocodeinonesemicarbazone

The method of Example 6 was followed except that 3.0 g of 14-OH-dihydrocodeinone were used as starting material. 3.2 g of crude product were obtained, which is a mixture of the syn and anti isomers according to thin-layer chromatographic examinations. After recrystallization from a mixture of chloroform and ethanol, pure semicarbazone can be achieved. M.p.: 236°–238° C.

PMR (DMSO-d$_6$): 9.25s (NH; 1H), 6.8dd (H-1.2; 2H), 6.4s (NH$_2$;2H), 4.81s (H-5$\beta$; 1H), 3.75s (OCH$_3$; 3H), 2.3s (N-Me; 3H). The 5-$\beta$-H shifts in the crude product comprising the isomers in a weight ratio of 1:1 are as follows: 4.85 (trans) and 5.17 (cis) ppm (CDCl$_3$). MS (C$_{19}$H$_{24}$N$_4$O$_4$-372.41) 372(25) 355(58) 313(70)

EXAMPLE 8

14-OH-codeinone-semicarbazone

The method of the preceeding example was followed except that 3.0 g 14-OH-codeinone were used as starting material. 2.8 g of crystalline crude product are formed, which is a mixture of the syn and anti isomers according to thin-layer chromatographic examinations. After recrystallization from methanol, a uniform product can be achieved. M.p.: 260°–263° C. (dec.)

PMR (CDCl$_3$): 8.72s (NH; 1H), 6.7dd (H-1.2; 2H), 6.3d (H-8; 1H), 5.85d (H-7; 1H), 5.19s (H-6$\beta$; 1H; trans), 5.0s (NH$_2$; 2H 3.8s (OCH$_3$; 3H), 2.4s (N-CH$_3$; 3H) MS (C$_{19}$H$_{22}$N$_4$O$_4$-370.40) 370(35) 353 (22) 313(29)

EXAMPLE 9

Codeinone semicarbazone 1.2 g semicarbazide chlorohydrate are dissolved in 50 ml of water and the solution is heated on a water bath for a hour after the addition of 3.0 g of codeinone. After cooling to +5° C., the solution is alkalified by concentrated sodium carbonate solution (pH~9-10), and the separated oil is extracted with 3×30 ml of chloroform. The chloroform phase is washed with saline, dried over magnesium sulfate and evaporated off. The residue is crystallized from ethanol and small chloroform. The melting point of codeinon semicarbazone (1.3 g) is the same as referred to in the prior art [Knorr, L., Hörlein, H.: Ber. 40 2032 (1407)], but it gives two spots on a chromatoplate. According to the PMR spectra the product is the mixture of the syn and anti isomers.

PMR (CDCl$_3$): 8.75s (NH; 1H), 6.7m (H-1.2; 2H), 6.2dd (H-8; 1H), 5.85dd (H-7; 1H), 5.2s (H-5$\beta$; 1H; trans), 3.8s; 3.81s (OCH$_3$; 3H), 2.4s (N-Me; 3H) MS (C$_{19}$H$_{22}$N$_4$O$_3$-354.40) 354(100) 337(23)

EXAMPLE 10

14-OH-dihydromorphinone semicarbazone

The procedure of Example 6 was followed except that the reaction was carried out within 2 hours. 2.5 g of semicarbazone were obtained from 3.0 g of 14-OH-dihydromorphinone, which proved to be homogenous upon examining by thin-layer chromatography. The melting point of the product is 217°–220° C. after recrystallization from ethanol.

PMR (CDCl$_3$): 8.35s (NH; 1H), 6.6dd (H-1.2; 2H), 6.0s (NH$_2$; 2H), 4.93s (H-5$\beta$; 14; trans), 2.3s (N-Me; 3H) MS (C$_{18}$H$_{22}$N$_4$O$_4$- 358.39) 358(5) 327(49)

EXAMPLE 11

Dihydromorphinone semicarbazone

The procedure of Example 10 was followed except that 2.85 g of dihydromorphinone were used as starting material. 3.2 g of dihydromorphinone semicarbazone were obtained, which gave more spots upon examining by thin-layer chromatography (eluent:eluent systems A and B). The minor impurity component could be removed by recrystallization from methanol and a homogenous product could be achieved. M.p.: 195°–198° C.

PMR (DMSO-d$_6$): 6.6dd (H-1.2; 2H); 6.4s (NH$_2$; 2H), 4.9s (H-5$\beta$; 1H), 2.3s (N-Me; 3H), The 5-$\beta$ protons' shifts in the crude product comprising the trans and cis isomer in a weight ratio of 71:29 are as follows: 4.9 (trans) and 5.34 (cis) ppm. MS (C$_{18}$H$_{22}$N$_4$O$_3$-342.39) 342(58) 325(85) 283(86)

EXAMPLE 12

Naloxon semicarbazone

The procedure of Example 10 was followed except that 0.65 g of Naloxon and 0.25 g of semicarbazide chlorohydrate were used as starting materials. 0.5 g of Naloxon semicarbazone were formed, which proved to be homogenous upon examining by thin-layer chromatography. M.p.: 239°–242° C. (dec.)

PMR (DMSO-d$_6$): 9.15s (NH; 1H), 6.45dd (H-1.2; 2H), 5.8m (allyl-proton; 1H), 5.0-5.2m (allyl-proton; 2H), 4.75s (H-5$\beta$; 1H) MS (C$_{20}$H$_{24}$N$_4$O$_4$-384.42) 384(6) 298(12)

EXAMPLE 13

Naloxon methylether semicarbazone

In 15 ml of water 0.25 g of semicarbazide chlorohydrate are dissolved and 0.68 g of Naloxon-methylether are added, then the solution is heated on a water bath for two hours. After cooling the solution is made alkaline by adding a concentrated sodium carbonate solution (pH~9), the crystalline substance is filtered off, and washed with water. 0.6 g of crude product are obtained, which gives two spots upon examining by thin-layer chromatography. The two spots are the syn and anti isomers. PMR (DMSO-$d_6$): The $OCH_3$ group has two signs (3.75 ppm). The shifts of the $5\beta$ protons are as follows: 4.70 (trans) and 4.82 (cis) ppm. Weight ratio of the isomers: 21:79.

MS ($C_{21}H_{26}N_4O_4$-398.45)

EXAMPLE 14

Dihydrotebainone semicarbazone

The procedure of Example 6 was followed except that 3.0 g of dihydrotebainone were used as starting material 2.7 g of crude dihydrotebainone semicarbazone are obtained which are homogenous upon examining by thin-layer chromatography. The melting point of the product is 226°-227° C. after recrystallization from ethanol.

PMR (CDCl$_3$): 8.48s (NH; 1H), 6.65dd (H-1.2; 2H), 6.15s (NH$_2$; 2H), 3.8s (OCH$_3$; 3H), 2.4s (N-Me; 3H) MS ($C_{19}H_{26}N_4O_3$-358.43) 358(42) 341(23) 299(100)

EXAMPLE 15

Dihydrocodeinone thiosemicarbazone 3.0 g of dihydrocodeinone are suspended in 15 ml of water, thereafter it is dissolved with the aid of 10 ml of 1N hydrochloric acid. 1.0 g of thiosemicarbazide is added, and the solution is heated on a water bath for two hours. The hot solution is filtered off and the dihydrocodeinon thiosemicarbazon hydrochloride salt (4.0 g) quickly precipitates. This salt is recrystallized from water. M.p.: at 210° C. the product becomes yellow and decomposes between 250°-255° C. The hydrochloric salt is dissolved in water (1.0 g in 100 ml of water) and the base is liberated by adding a concentrated sodium carbonate solution (pH~9). This product is filtered and washed with water. The product is a mixture of steric isomers according to the PMR spectra.

PMR (DMSO-$d_6$): 10.32s (NH; 2H cis and trans) 8.32s (NH$_2$; 2H cis and trans), 7.75s (NH$_2$; 1H cis), 7.45s (NH$_2$; 1H trans), 6.6-6.75m (H-1.2), 5.45s (H-5$\beta$; 1Hc); 4.87s (H-5$\beta$; 1Ht), the isomer ratio is 63:37==trans:cis. MS ($C_{19}H_{24}N_4O_2S$-372(29) 355(17) 297(20) 242(48)

EXAMPLE 16

14-OH-dihydrocodeinone thiosemicarbazone 3.1 g of 14-OH dihydrocodeinone are transformed into 4.2 g of 14-OH-dihydrocodeinone thiosemicarbazone hydrochloride according to the method of Example 15.

The hydrochloride salt well crystallizes from water, its melting point (capillary) is 230°-235° C. (decomp.).

The melting point of the base is 150°-154° C. (decomp.).

PMR (CDCl$_3$): 8.63s (NH; 1H), 7.48s (NH$_2$; 1H), 6.65dd (H-1.2; 2H), 6.4s (NH$_2$; 1H), 4.92s (H-5$\beta$; 1H), 3.8s (OCH$_3$; 3H), 2.35s (N-Me; 3H). Pure trans isomer. MS ($C_{19}H_{24}N_4O_3S$-388.47) 388)72) 371(100) 313 (42)

EXAMPLE 17

14-OH-codeinone thiosemicarbazone

According to the method described in Example 15 3.7 g of 14-OH-codeinone-thiosemicarbazone hydrochloride are prepared from 3.1 g of 14-OH-codeinone. After recrystallization from water it melts at 290°-295° C. (decomposition).

The melting point of the base is 233°-234° C. (dec.).

PMR (DMSO-$d_6$): 10.15s (NH; 1H), 8.48s; 7.95s (NH$_2$; 2H), 6.6dd (H-1.2; 2H), 6.25d (H-7; 1H), 6.05s (H-8; 1H), 5.87 (H-5$\beta$; 1H), 3.7s (OCH$_3$; 3H), 2.35s (N-CH$_3$; 3H), MS ($C_{19}H_{22}N_4O_3S$-386.46): 386(100); 369(50) 311(43)

EXAMPLE 18

Dihydromorphinone thiosemicarbazone

According to the method described in Example 15, 2.5 g of dihydromorphinone thiosemicarbazone hydrochloride are prepared from 2.8 g of dihydromorphinone. Though the endproduct well crystallizes from water, it does not have a defined melting point.

After several recrystallization of the hydrochloric salt, the base is prepared. On the basis of thin-layer chromatographic examinations (eluent: A or B solvent mixture) the base comprises two components.

PMR (DMSO-$d_6$): 10.41s (NH; 1H cis), 10.32s (NH; 1H trans), 9.10s (C$_3$-OH), 8.25s (NH$_2$; 2H cis and trans), 7.67s (NH$_2$; 1H cis), 7.52s (NH$_2$; 1H trans) 6.55s (H-1.2; 2H), 5.45s (H-5$\beta$; 1H cis), 4.85s (H-5$\beta$; 1H trans) 2.3s (N-Me; 3H) isomer ratio is 69:31=trans:cis. MS ($C_{18}H_{22}N_4O_2S-358.45$)

EXAMPLE 19

14-OH dihydromorphine thiosemicarbazone

According to the method of Example 15 2.8 g of 14-OH-dihydromorphinone thiosemicarbazone hydrochloride are prepared from 3.0 g of 14-OH-dihydromorphine. The hydrochloride salt does not have a defined melting point even after several recrystallization from water. The base comprises two components according to thin-layer chromatographic analysis. The base well crystallizes from ethanol or methanol, but it is not homogenous upon examining by thin-layer chromatography.

PMR (DMSO-$d_6$): 10.18s (NH; 2H cis+trans) 8.32s (NH$_2$; 2H; cis+trans) 7.65s (NH$_2$; 1H cis) 7.55s (NH$_2$; 1H trans) 5.33s (H-5$\beta$; 1H cis), 4.76s (H-5$\beta$; 1H trans), 2.3s (N-Me; 3H) isomer ratio: cis/trans 21/79. MS ($C_{18}H_{22}N_4O_3S$-374.45)

EXAMPLE 20

Dihydrocodeinone phenylhydrazone 1.5 g of dihydrocodeinone are dissolved in 30 ml of dry ethanol, then 1.5 ml of freshly distilled phenylhydrazine and 1.0 ml of glacial acetic acid are added. The solution is boiled on a water-bath for 30 minutes, thereafter cooled and made alkaline by concentrated ammonium hydroxyde. The product quickly crystallizes.

PMR (CDCl$_3$): 7.3-6.8m (C$_6$H$_5$; 5H), 6.7dd (H 1.2; 2H), 5.13s (H-5$\beta$; 1H), 3.8s (OCH$_3$; 3H), 2.35s (N-Me; 3H), pure trans isomer. MS ($C_{24}H_{27}N_3O_2$-389.48) 389(90) 252(8) 212(15)

EXAMPLE 21

14-OH-dihydrocodeinone phenylhydrazone

Using 1.55 g of 14-OH-dihydrocodeinone as starting material 1.7 g 14-OH-dihydrocodeinone phenylhydrazone were prepared according to the procedure used for the preparation of dihydrocodeinone phenylhydrazone. After recrystallization from ethanol, the product melts at 174°–176° C.

PMR (CDCl$_3$): 9.5s (NH; 1H), 7.3-7.0m (C$_6$H$_5$; 5H), 6.7dd (H-1.2; 2H), 5.37s (H-5$\beta$; 1H), 4.9s (OH; 1H), 3.75s (OCH$_3$; 3H), 2.4s (N-Me; 3H), pure cys isomer. MS (C$_{24}$H$_{27}$N$_3$O$_3$-405.48) 405(100) 386(7) 228(17)

EXAMPLE 22

14-OH-codeinone phenylhydrazone

Using 1.55 g of 14-OH-codeinone as starting material 1.4 g of 14-OH-codeinone phenylhydrazone was prepared according to the method of Example 20. The product well crystallizes from ethanol. M.p.: 192°–194° C. The product is sensitive to light, it turns to yellow due to the effect of light.

PMR (CDCl$_3$): 8.75s (NH; 1H), 7.3-6.9m (C$_6$H$_5$; 5H), 6.7dd (H-1.2; 2H), 6.45d (H-8; 1H), 5.7d (H-7; 1H), 5.42s (H-5$\beta$; 1H cis), 3.75s (OCH$_3$; 1H), 2.4s (N-Me; 3H) MS (C$_{24}$H$_{25}$N$_3$O$_3$-403.46) 403(8) 385(77) 370 (13)

EXAMPLE 23

Dihydromorphinone phenylhydrazone 1.4 g of dihydromorphinone and 1.3 ml of freshly distilled phenylhydrazone are dissolved in 30 ml of dry ethanol, thereafter refluxed for 30 minutes. The ethanol is distilled off, then the residual red oil is triturated with ether. The crystalline substance thus obtained is filtered off, washed with ether and small cold ethanol. 1.0 g of dihydromorphinone phenylhydrazone is obtained which is composed of two components according to thin-layer chromatographic examinations (eluent: A or B eluent mixture). According to PMR analysis the two components are the syn and anti isomers (trans/cis=28/72).

PMR (DMSO-d$_6$): 9.67 s (NH; 1H cis), 8.82 s (NH; 1H trans) 7.3-7.0 m (C$_6$H$_5$; 5H), 6.6-6.7 m (H-1.2), 5.4 s (H-5$\beta$; 1H; cis), 5.12 s (H-5$\beta$; 1H; trans), 2.4 s (N-Me; 3H), MS (C$_{23}$H$_{25}$N$_3$O$_2$-375.45) 375(100) 283(19) 212(20)

EXAMPLE 24

14-OH-dihydromorphinone phenylhydrazone 1.2 g of 14-OH-dihydromorphinone phenylhydrazone were prepared according to the method of Example 23 starting from 1.5 g of 14-OH-dihydromorphinone. The product is composed of two components, they proved to be the syn and anti isomers.

PMR (CDCl$_3$): 9.3 s (NH; 1H), 7.2-7.0 m (C$_6$H$_5$), 6.7-6.5 m (H-1.2; 2H), 5.3 s (H-5$\beta$; 1H; cis) 5.05s (H-5$\beta$; 1H; trans) 2.3s (N-Me; 3H), MS (C$_{23}$H$_{25}$N$_3$O$_3$-391.45) 391(100)

EXAMPLE 25

Dihydrocodeinone-2,4-dinitro-phenylhydrazone 1.0 g of 2,4-dinitrophenyl hydrazine is dissolved in 40 ml of concentrated hydrochloric acid, thereafter 200 ml of water and 1.5 g of dihydrocodeinone are added (hot). The mixture is slightly boiled for 5 minutes, thereafter left to cool. The yellow dihydrocodeinone-2,4-dinitrophenyl hydrazone hydrochloride quickly crystallizes. The weight of the product is 2.3 g after filtration and washing with cold water. The base can be precipitated from the diluted aqueous solution of the hydrochloric salt with the aid of concentrated sodium carbonate solution (pH ~9). The melting point of the base is 207°–208° C. after crystallization from ethanol or n-propanol.

PMR (CDCl$_3$): 12.85s (NH; 1H), 9.1d (Ar-H; 1H), 8.25dd (Ar-H; 1H), 7.9d (Ar-H; 1H), 6.7dd (H-1.2; 2H), 5.32s (H-5$\beta$; 1H cis), 3.75s (OCH$_3$; 3H), 2.4s (N-Me; 3H) MS (C$_{24}$H$_{25}$N$_5$O$_6$-479.48) 479(100) 462(M-17; 20)

EXAMPLE 26

14-OH-dihydrocodeinone-2,4-dinitrophenyl hydrazone

The method of the preceeding example is followed. 2.1 g of 14-OH-dihydrocodeinone-2,4-dinitrophenyl hydrazone hydrochloride are obtained from 1.55 g of 14-OH-dihydrocodeinone. The base can be crystallized from a mixture of chloroform and ethanol. M.p.: 232°–233° C.

PMR (CDCl$_3$): 12.8s (NH; 1H), 9.15d (Ar-H; 1H), 8.33dd (Ar-H; 1H), 7.9d (Ar-H; 1H), 6.75dd (H-1.2; 2H), 5.33s (H-5$\beta$; 1H cis), 3.8s (OCH$_3$; 3H), 2.4s (N-Me; 3H), Ms (C$_{24}$H$_{25}$N$_5$O$_7$-49.548) 495(40) 478(M-17; 16)

EXAMPLE 27

14-OH-codeinone-2,4-dinitrophenyl hydrazone

The method of Example 25 is followed except that 1.55 g of 14-OH-codeinone is used as starting material. 2.2 g of 14-OH-codeinone-2,4-dinitrophenyl hydrazone hydrochloride are obtained. The base liberated from the salt crystallizes from ethyl acetate, mp.: 157°–160° C.

PMR (CDCl$_3$): 12.15s (NH; 1H), 9.2d (Ar-H; 1H), 8.44dd (Ar-H; 1H), 7.95d (Ar-H; 1H), 6.7dd (H-1.2; 2H), 6.5d (H-8; 1H), 6.1d (H-7; 1H), 5.43s (H-5$\beta$; 1H cis), 3.8s (OCH$_3$; 3H), 2.4s (N-Me; 3H) MS (C$_{24}$H$_{23}$N$_5$O$_7$-493.46) 493(27) 476(M-17; 10)

EXAMPLE 28

Codeinone-2,4-dihydrophenyl hydrazone 1.2 g of codeinone and 0.9 g of 2,4-dinitrophenyl hydrazine are stirred in 20 ml of 96% of acetic acid on a water bath for 30 minutes. The mixture is cooled (0°–5° C.) and alkalified by concentrated ammonium hydroxide solution (pH 9). The precipitated oil is extracted with 3×25 ml of chloroform. The chloroformic solution is washed with brine and dried over magnesium sulfate. After evaporation of the solvent the yellow crystalline residue (1.3 g) is crystallized from a mixture of ethanol and chloroform. Weight: 0.75 g M.p.: 259°–261° C.

PMR (CDCl$_3$): 12.18s (NH; 1H), 9.2d (AR-H; 1H), 8.4dd (Ar-H; 1H), 7.95d (Ar-H; 1H), 6.7dd (H-1.2; 2H), 6.35dd (H-; 1H), 6.05dd (H-; 1H), 5.43s (H-5$\beta$; 1H cis), 3.8s (OCH$_3$; 3H), 2.3s (N-Me; 3H) MS (C$_{24}$H$_{23}$N$_5$O$_6$-477.46) 477(100) 460 (M-17; 8)

EXAMPLE 29

Dihydromorphinone-2,4-dinitrophenyl hydrazone

According to the method of Example 25 2.0 g of dihydromorphinone-2,4-dinitrophenyl hydrazone hydrochloride are prepared from 1.4 g of dihydromorphinone. The base liberated from the salt is composed of two components, it is the mixture of the syn and anti isomers according to thin-layer chromatographic analysis (eluent: A and B eluent system).

The two isomers cannot be separated either by crystallization (ethanol or methanol) or chromatographically (column chromatography or preparative thin-layer chromatography). The recrystallization of the hydrochloride from water does also not give the desired result.

PMR (CDCl$_3$): 13.17s (NH; 1H; cis), 11.10s (NH; 1H, trans) 9.15dd (Ar-H; 1H), 8.25dd (Ar-H; 1H), 6.7m (H-1.2; 2H), 5.35s (H-5$\beta$; 1H cis), 5.07s (H-5$\beta$; 1H trans), 2.4s (N-Me; 3H) cis-trans ratio 27:73. MS (C$_{23}$H$_{23}$N$_5$O$_6$-465.35) 465(63) 448(M-17; 12) 431(M-34; 34)

EXAMPLE 30

14-OH-dihydromorphinone-2,4-dinitrophenyl hydrazone

According to the method of Example 25 1.5 g of 14-OH-dihydromorphinone-2,4-dinitrophenylhydrazone hydrochloride are prepared from 1.5 g of 14-OH-dihydromorphinone.

The precipitated base is composed of two components according to thin-layer chromatographic analysis. The two isomers (syn and anti) cannot be separated either by crystallization or preparative thin-layer chromatography.

PMR (CDCl$_3$): 13.1s (NH; 1H trans), 11.15s (NH; 1H cis) 9.2m (Ar-H), 8.3m (Ar-H), 8.1d and 7.9d (Ar-H), 6.7m (H-1.2), 5.38s (H-5$\beta$; trans), 5.10s (H-5$\beta$; cis) PMR (C$_6$D$_6$) 12.95s (NH; trans) 10.60s (NH; cis) 8.8d; 8.6d (Ar-H), 7.8m (Ar-H), 7.65d; 7.4d (Ar-H), 6.8m (H-1.2), 5.03s (H-5$\beta$; cis), 4.73s (H-5$\beta$; trans) isomer ratio trans/cis=60/40. MS (C$_{23}$H$_{23}$N$_5$O$_7$-481.45) 481(62) 464(M-17; 18), 447(M-34; 32)

We claim:

1. The compounds: 14-OH dihydromorphinone phenylhydrazone, 14-OH-dihydromorphinone-2,4-dinitrophenyl hydrazone, and the steric isomers and the pharmaceutically acceptable salts thereof.

2. Analgetic and morphine-antagonistic pharmaceutical formulation which comprises an analgesically effective amount of at least one compound of the formula (I) of claim 1, the steric isomers or the pharmaceutically acceptable salts claim 1 in association with at least one excipient.

* * * * *